(12) United States Patent
Zucchelli et al.

(10) Patent No.: US 9,821,306 B2
(45) Date of Patent: Nov. 21, 2017

(54) DEVICES AND METHODS FOR PROGRAMMABLE MANIPULATION OF PIPETTES

(75) Inventors: Piero Zucchelli, Versonnex (FR); Giorgio Horak, Geneva (CH); Antoine Jordan, Geneva (CH)

(73) Assignee: Andrew Alliance S.A., Vernier (CH)

( * ) Notice: Subject to any disclaimer, the term of this patent is extended or adjusted under 35 U.S.C. 154(b) by 869 days.

(21) Appl. No.: 13/881,965

(22) PCT Filed: Nov. 22, 2011

(86) PCT No.: PCT/IB2011/003037
§ 371 (c)(1),
(2), (4) Date: Jul. 8, 2013

(87) PCT Pub. No.: WO2012/069925
PCT Pub. Date: May 31, 2012

(65) Prior Publication Data
US 2013/0280143 A1 Oct. 24, 2013

Related U.S. Application Data

(60) Provisional application No. 61/416,546, filed on Nov. 23, 2010.

(51) Int. Cl.
*B01L 3/02* (2006.01)
*B01L 9/00* (2006.01)
*G01N 35/00* (2006.01)
*G01N 35/02* (2006.01)
(Continued)

(52) U.S. Cl.
CPC .............. *B01L 3/021* (2013.01); *B01L 3/0237* (2013.01); *B01L 9/54* (2013.01); *B25J 9/1697* (2013.01);
(Continued)

(58) Field of Classification Search
CPC ........ B01L 3/02; B01L 3/0227; B01L 3/0237; B01L 2300/02
See application file for complete search history.

(56) References Cited

U.S. PATENT DOCUMENTS 5,443,790 A 8/1995 Coeurveille et al.
2003/0215360 A1* 11/2003 Ruddock ............... B01L 3/0279
422/63
(Continued)

FOREIGN PATENT DOCUMENTS

JP S61-142088 A 6/1986
JP S62-254034 A 11/1987
(Continued)

*Primary Examiner* — Jan Ludlow
(74) *Attorney, Agent, or Firm* — Burns & Levinson LLP; John C. Serio

(57) ABSTRACT

The present invention is directed generally to devices and methods for manipulating laboratory pipettes in a programmable manner. The present invention is directed to an apparatus and methods for allowing a user to instruct the device to perform a specific process; identifying the type, location and identity of the consumables to be used; manipulating a plurality of pipettes for performing the liquid handling; monitoring the process during and after its execution; generating a detailed report for the plurality of actions. Other aspects of this invention include optimization of the liquid dispensing performances of a pipette; monitoring and controlling individual actions by means of vision; virtualization of the protocol definition by means of a reality augmented software interface; integration of the system in a conventional laboratory environment workflow.

10 Claims, 11 Drawing Sheets

(51) Int. Cl.
  *G01N 35/10* (2006.01)
  *B25J 9/16* (2006.01)
(52) U.S. Cl.
  CPC ... *G01N 35/0099* (2013.01); *G01N 35/00732* (2013.01); *G01N 35/026* (2013.01); *G01N 35/028* (2013.01); *G01N 35/1011* (2013.01); *G01N 35/1016* (2013.01); *B01J 2219/00364* (2013.01); *B01J 2219/00693* (2013.01); *B01J 2219/00698* (2013.01); *B01L 2200/0621* (2013.01); *B01L 2200/087* (2013.01); *B01L 2200/14* (2013.01); *B01L 2200/143* (2013.01); *G01N 2035/00752* (2013.01); *G01N 2035/00782* (2013.01); *G01N 2035/00792* (2013.01); *G01N 2035/103* (2013.01); *G01N 2035/1048* (2013.01)

(56) References Cited

U.S. PATENT DOCUMENTS

2005/0203824 A1   9/2005  Freud et al.
2005/0278199 A1  12/2005  Ghani
2006/0105359 A1   5/2006  Favuzzi et al.
2007/0177778 A1   8/2007  Massaro
2007/0203823 A1   8/2007  Whelchel et al.
2007/0293997 A1  12/2007  Couch
2009/0055131 A1*  2/2009  Bukshpan ............ B01L 3/02
                                                  702/187
2011/0160909 A1*  6/2011  Glauser ......... G01N 35/00722
                                                  700/264

FOREIGN PATENT DOCUMENTS

| | | |
|---|---|---|
| JP | S63-034093 | 2/1988 |
| JP | H04-323562 A | 11/1992 |
| JP | H05-240868 A | 9/1993 |
| JP | H06-050981 A | 2/1994 |
| JP | 2003-092749 A | 3/2003 |
| JP | 2004-001153 A | 1/2004 |
| JP | 2005-533669 A | 11/2005 |
| JP | 2006-170786 | 6/2006 |
| JP | 2007-024537 A | 2/2007 |
| JP | 2009-525467 A | 7/2009 |
| WO | 2004009300 A1 | 1/2004 |

* cited by examiner

DEVICES AND METHODS FOR PROGRAMMABLE MANIPULATION OF PIPETTES

CROSS-REFERENCE TO RELATED APPLICATION DATA

This application claims the benefit of U.S. Provisional Patent Application Ser. No. 61/416,546, filed on Nov. 23, 2010, the contents of which are incorporated herein by reference in its entirety.

FIELD OF THE INVENTION

The present invention relates to the field of automation of chemical, biological, and biochemical processes or reactions. More specifically, it discloses devices and methods for manipulating pipettes in a programmable manner.

BACKGROUND OF THE INVENTION

Traditionally and historically, liquid handling constitutes a fundamental building block of most biochemical, chemical and biological tests performed across multiple industries.

Liquid handling is essentially defined as the operations of putting one sample in contact with another one, sometimes in a repetitive way, being able to quantify the amount of at least one of the two samples to be used. Despite the fact that a narrow definition of liquid strictly indicates materials in the liquid form, hereafter we refer to liquid handling the generic operation of handling materials in the solid (for example powders), liquid or gaseous form—or in any mixture of these states (for example, heterogeneous samples containing solid and liquids mixed together like cell cultures and emulsions or gases and liquids mixed together like gels).

In the liquid handling arena, most solutions can be characterized by different degrees of performances, where the performances are defined according different aspects which are of interest to the user, and constitute a reason for utility: for example, flexibility, ease of use, throughput, reproducibility, traceability, and cost-effectiveness. Flexibility is defined as the capability of dealing with heterogeneous processes, over a wide range of volumes and for different characteristics of the liquids, but also in respect to other properties and requirements. Ease of use is defined as the quality of requiring minimal training for its adoption, and a faster and intuitive translation of the user intent into the proper and desired operation. In particular, the translation of the user intent to perform a desired operation—without requiring a direct involvement during its execution—is also referred to as programmability. Throughput is defined as the amount of independent, partially dependent or dependent processes that can be performed within a suitable unit of time. Reproducibility is defined as minimal variations between different implementations of the same protocol for any reason. Reproducibility can be evaluated for protocols performed simultaneously or at a different moments by the same operator or device, but it can also include variations introduced by different operators or different devices—in particular when evaluated with respect to the target performances as defined by the user, also referred to as precision. For example, lack of precision in a biological process can be generated by a slow clock used for the timing of the liquid handling steps—or by an incorrect calibration of the volumetric scale of the liquid handling device. Traceability is defined as the property of keeping record, for a-posteriori analysis and verification, of the actual process that has been implemented, including unpredictable events during the protocol execution like possible faults or mistakes. Cost effectiveness is defined as the weighted sum of the cost components in the acquisition of a liquid handling apparatus, user training, cost of consumables, cost of maintenance, cost of operations, cost of repair and cost of dismissal at the end of its lifetime.

Liquid handling today is performed either manually by human operators, or by means of automatic devices of various types.

In the most conventional laboratory environment, liquid handling is performed by means of tools—defined as pipettes—allowing for a quantitative estimation of the sample being transported. In the case of liquids, a common practice is to estimate the amount of sample by means of its volume. Therefore, manual liquid handling is typically performed by means of volumetric adjustable pipettes capable of transporting liquid from one recipient to another in a known amount pre-defined by an operator. Hereafter we define as pipette the liquid handling tool available and initially foreseen for the procedures of manual liquid handling, or at least partially conceived for this application or simply inspired to the tool used for this purpose. It should also be mentioned that two types of pipettes are commercially available: electronic pipettes and mechanical pipettes. While electronic pipettes present some advantages in terms of calibration and ergonomics, mechanical pipettes still represent a large fraction of the market, being economical, performing, robust, cheaper and simple to operate. Above all, they've become an industry standard tool responding to very precise norms, for example ISO 8655 normatives. The difference in ergonomics is mainly related to the force to be applied by the operator thumb (defined also as thumb action) on the pipette itself, for example for the purpose of liquid aspiration, dispensing, mixing, and tip ejection. The overall set of procedures involving a pipette is hereafter referred to as manipulation of the pipette.

In most cases, for the purpose of avoiding contamination, pipettes are typically interfaced to the sample by means of tips, which are consumables meant to avoid a direct contact of the pipette itself with the liquid—that otherwise will unavoidably transport undesired molecules to undesired places. The use of tips has become a standard practice in industrial and research environments, with multiple types available and chosen by customers according to their maximum volume, presence of filters, surface absorption properties of molecules, materials, brands and ultimately cost. Pipette tips can be considered specific pipette accessories or in alternative as part of a larger class of laboratory devices defined as consumables, that include among others microplates, tubes, Eppendorf tubes, microtubes, vacutainers, filters, containers, capsules, vials and bottles typically used in the field of liquid handling and biological or chemical reactions.

In recent years, the pharmaceutical, biotechnology, chemical, healthcare and related industries have increasingly adopted automated solutions for performing various reactions and analyses. The benefits of these automatic devices include reproducibility, speed, capacity and ultimately cost reductions at high throughput, enabling some users to perform a large number of reactions with limited human intervention, typically performing multiple reactions in parallel.

Automatic devices are usually associated to laboratories which require large production capacity—since their size, cost and complexity of operations induce users adopting them when a significant number of processes to be performed. However, sometimes automatic devices are also used in low and medium throughput environments, when the features of reproducibility and traceability are strictly required—like in the sector of healthcare and diagnostics.

Examples of applications in the sector of healthcare consists in the processing of heterogeneous biofluids, defined as biological or chemical fluids which present different components which are visually selectable at the macroscopic level. A known example consists of processing separated blood, for example following fractionation, with the purpose of separating buffy coat from erythrocytes and plasma (or serum). Extraction of the buffy coat from the tube by manual pipetting is a very unreliable, imprecise, difficult and time consuming operation. Therefore, blood banks employ dedicated automated systems of large complexity, like the one described by Quillan et al. (International Journal of Epidemiology 2008; 37:i51-i55) which are addressing the need of precise and reproducible operations at high throughput. However, also smaller clinical environments, like hospitals and analysis laboratories, dealing with a smaller number of patient samples would profit of the same advantages of reproducibility at a more limited throughput.

Cost of automatic devices is often linked to their mechanical complexity: precise and reproducible movements over a large area require precision mechanics, including undeformable metallic frames determining a significant weight, ultimately making these systems not transportable and expensive to manufacture. Weight and dimensions has also a significant impact on the cost of operations, since maintenance, repairs, training and upgrades have to be performed by specialized personnel on-site. And heavy systems imply stronger motors and higher electrical current absorption, making their design more complex and expensive to produce. Not to speak about portability of the devices and an easy integration into an existing laboratory.

Among others, a crucial requirement of a liquid handling process is its actual reproducibility with respect to state-of-art validated protocols. Since most of the assay development is performed by means of manual liquid handling, it is obvious that results emerging from manual liquid handling often constitute the reference for a given liquid handling system. However, it is well known to those skilled in the art (for example, Pandya et al.—Journal of Pharmaceutical and Biomedical Analysis 53, 2010, pg. 623-630) that manual liquid handling misses in particular traceability, precision and reproducibility. This is partially taken care by tools calibration and performances, since above all it is consequence of the human nature and the propagation of instructions between humans, training included. In addition, the low acquisition cost of manual liquid handling tools should not hide the significant cost of operations generated by the necessity of having human operators. This is particularly true since it also emerged that repetitive operations involving pipettes introduce a significant strain on the muscoskeletal system, with possible consequence of work-related diseases. So, the potential productivity of one operator has to be limited to minimize the risk of occurrence of different pathologies, like cumulative trauma disorders (CTDs) and repetitive strains injuries (RSIs). Obviously, it would be desirable to remove these risks completely from the professional environment—however the straight replacement of humans with automatic liquid handling systems clashes against the need of flexibility, which is required in various activities, but also collides with economic considerations due to the significant initial cost to be undertaken for the adoption and operation of automated infrastructure. In summary, there is the current evidence of a gap between manual liquid handling operations and automatic liquid handling systems—which ultimately address in different ways liquid handling targets but do not overlap in utility. The present inventions address this gap, providing a useful tool to research environments and industry.

Another crucial requirement of a liquid handling system consists in its transportability, and a small space usage in a laboratory. Transportability enables a lower final cost to the user, avoiding on-site installation of the system and on-site support and maintenance. A system with a small footprint and light weight allows its installation in a conventional laboratory environment without the need of specific infrastructure, and better integration into the existing laboratory workflow. A light system additionally absorbs less electrical current, enabling the possibility of battery or solar power in those areas where electrical supply is limited.

As pipettes, including state-of-art design solutions for the purpose of manual liquid handling, a summary of some of the prior art includes:

Gilson et al. (U.S. Pat. No. 3,827,305) teach a hand-help pipette with adjustable volume mechanism;

Magnussen et al. (U.S. Pat. No. 4,905,526) teach an electrically assisted pipette;

Scordato et al. (U.S. Pat. No. 4,821,586) teach an example of computer controlled pipette;

Gilson et al. (U.S. Pat. No. 6,158,292) teach a tip ejection system for a liquid handling pipette;

Cronenberg et al. (U.S. Pat. No. 6,977,062) teach an automatic tip removal system including tip identification methods.

As automatic liquid handling systems, their engineering solutions and their conceptual design, a summary of some of the prior art is as follows:

Gilman et al. (U.S. 2003/0225477) disclose a modular equipment apparatus and methods for handling labware Pfost et al. (U.S. Pat. No. 5,104,621) disclose an automated multi-purpose analytical chemistry processing center and laboratory workstation.

Shumate et al. (U.S. Pat. No. 6,372,185) disclose a liquid chemical distribution method and apparatus Bjornson et al. (U.S. 2006/0127281) disclose a pipetting apparatus with integrated liquid level and/or gas bubble detection.

Kowalski et al. (U.S. Pat. No. 5,139,744) disclose an automated laboratory workstation having module identification means.

As other solutions, integrating automation into dedicated systems at low throughput, or describing dedicated systems to specific applications, the prior art includes:

Zucchelli et al. (U.S. Pat. No. 7,152,616) teach devices and methods for programmable microscale manipulation of fluids;

Blanton et al. (U.S. Pat. No. 7,601,300) teach a compact integrated system for processing test samples at low throughput in a diagnostics environment.

Clark et al. (U.S. Pat. No. 5,482,861) teach an automated continuous and random access analytical system;

Wegrzyn et al. (U.S. 2004/0241872) teach an optical detection liquid handling robot system;

Ruddock et al. (U.S. Pat. No. 7,105,129) teach a liquid handling robot for well plates using a powered anvil.

One drawback of prior art, in general, has been the difficulty to reconcile flexibility, in the form of fully programmable and configurable devices, with simplicity, in the form of low cost manufacturing and low cost operation, and reproducibility, characteristic of automated liquid handling systems.

The present invention meets the need for a flexible, reproducible, traceable, solution to perform liquid handling, at the same time improving the advantages of manual operations and introducing the benefits of automation at lower cost.

SUMMARY OF THE INVENTION

The present invention is directed towards an apparatus and methods for manipulating pipettes in a programmable manner: we define the systems and the devices exploiting those methods as liquid handling androids or simply androids.

Accordingly, in one aspect of the present invention, a plurality of pipettes is operated by an apparatus comprising a plurality of pipettes, at least one arm manipulating at least one pipette among the plurality of pipettes, and one software interface allowing to define the liquid handling protocol to be executed and governing the arm behaviour.

In another aspect of the present invention, it is disclosed a method for performing liquid handling by means of a manual pipette, which is operated automatically by means of a mechanical arm for the achievement of grabbing the suitable tip, setting the correct dispensing volume, aspirating a desired amount of liquid, dispensing a desired amount of liquid, ejecting the tip.

In yet another aspect of the present invention, a camera is used for the purpose of liquid handling by means of imaging a deck area from a plurality of angles and positions, simultaneously recognizing, measuring and localizing the consumables by means of their shape, dimensions, colour, height, barcode, distinctive features.

In another aspect of the present invention, the camera is integrated in the liquid handling apparatus and moving altogether with the arm controlling the pipette movements, enabling the use vision to identify the consumables and to exploit position information from the images to know precisely the relative position of the pipette against the consumable location.

In yet another aspect of the present invention, a device for processing biological or chemical fluids, comprising a deck area comprising a plurality of consumables in given locations, where the locations are assembled in a flexible and ordered configuration.

In another aspect of the present invention, a method for volumetric calibration of a pipette in a liquid handling android is achieved by dispensing a plurality of pre-set amounts of samples into at least one container, by evaluating the actual amount of samples being dispensed, and by incorporating into the software interface the notion of calibration without modifications to the pipette.

In another aspect of the present invention, a method for improving the volumetric reproducibility of a pipette in a liquid handling android is achieved by controlling the speed of the thumb action, modulated as a function of the volume, of the position of the pipette piston and of the category of liquid being used.

In another aspect of the present invention, a method for improving the volumetric reproducibility of a liquid handling android is achieved by including at least one sensor measuring humidity or temperature or pressure and refining the pipette calibration on the basis of the sensor information.

In another aspect of the present invention, a method for manipulating a pipette in a liquid handling android is achieved by means of measuring, preferentially a-priori but also in real-time, the thumb actuation pressure as a function of the thumb position, and afterwards controlling the thumb action only on the basis of the thumb position and speed.

In yet another aspect of the present invention, a method for manipulating a pipette comprises measuring the pressure of the thumb action as a function of the position of the thumb, and operating the thumb based on its position only.

In yet another aspect of the present invention, an apparatus for processing of biological or chemical fluids, the apparatus comprising a deck to host consumables wherein the deck is of a foldable type or of a self-assembling type.

In still yet another aspect of the present invention, a method for processing biological or chemical fluids, where a camera allows imaging a pipette tip, the same tip being partially transparent to light, wherein the camera can visualize the liquid inside the tip, and the image grabbed by the camera allows assessing the liquid volume contained in the tip, for the purpose of verification, volume determination, tracing and quality control.

In yet another aspect of the present invention, a method for processing heterogeneous biofluids like separated blood or separated milk or cell-containing fluids or beads-loaded liquids or suspensions or emulsions, where a mechanical arm allows manipulating a pipette, a camera allows imaging a pipette tip, a camera allows imaging the biofluid, wherein the relative position of the tip with respect to the various biofluid components is extracted from the image and used in order to control the aspiration and dispensing of a pipette in a certain location.

In still yet another aspect of the present invention, a method for processing biological or chemical fluids in a liquid handling android, comprising the simultaneous imaging of a pipette tip with respect to a consumable by means of a camera, and using the information from the image in order to determine the relative position in space of the tip with respect to the consumable in order to manipulate the pipette.

In yet another aspect of the present invention, a method for determining the liquid level in a container comprising the imaging of an object outside the liquid, and comparing the images of the same object while moving towards the liquid surface, wherein the change in the object images procured by the contact of the liquid with the object allows determining the location of the liquid level with respect to the object.

In yet another aspect of the present invention, a method for determining information about tips contained in a tip rack, comprising imaging the tip rack and identification of one or a plurality of tags within the rack, where the tags provide information about the number, location or type of tips within the rack.

These and other advantages, objects and features of the invention will be apparent through the detailed description of the embodiments and the drawings attached hereto. It is also to be understood that both the foregoing general description and the following detailed description are exemplary and not restrictive of the scope of the invention.

DETAILED DESCRIPTION OF THE INVENTION

The present invention relates to the manipulation of pipettes, as well as a number of its applications. For the purpose of illustration, the drawings as well as the description will generally refer to the apparatus addressing this solution as a liquid handling android. However, the means disclosed in this invention are equally applicable to more general embodiments in the field of liquid handling.

General Description of a Liquid Handling Android

The global structure of a liquid handling android comprises few elements, all of which have a given functional role in the architecture. In essence, a liquid handling android operates above a certain deck, that could include or not the android base itself. The deck could either be a physical part, soft or rigid, either a virtual region without delimitations—for example belonging to a laboratory bench. The deck could also be the physical assembly of smaller units, called blocks, that combine together in order to form a larger operating surface. A liquid handling android body—also referred to as base—provides the physical support to the arm, and possibly may comprise additional hardware like power chord connector, general switch, illumination, twister, settings camera, arm fixation, USB hub, tip waste tray, pipette rack, lifting handle. Most importantly, its purpose is providing a certain stable anchor to the arm movement. The arm constitutes the main electromechanical element: it generates movement of the hand in space, mainly moving over a two dimensional surface but also capable of lifting and descending the pipette in order to perform the desired pipette action. The arm is attached to the body and could either comprise a hand, or be connected to a hand. The hand constitutes the part of the body coming in contact with the pipette, and with the optional ability of grabbing and depositing pipettes onto the pipette rack. Additionally, the hand may contain a hand camera, the functionality of manipulating the pipette knob for the purpose of aspiration and dispensing, the functionality of tip ejection and the functionality of actuating the pipette for the purpose of setting a desired volume. The system is complemented by a software interface, whose purpose comprises controlling the movements of the arm, the actions of the hand, communicating with the cameras and processing the images, and above all managing all the interaction with the user for programmability purposes and also for reporting purposes.

Figure 1:
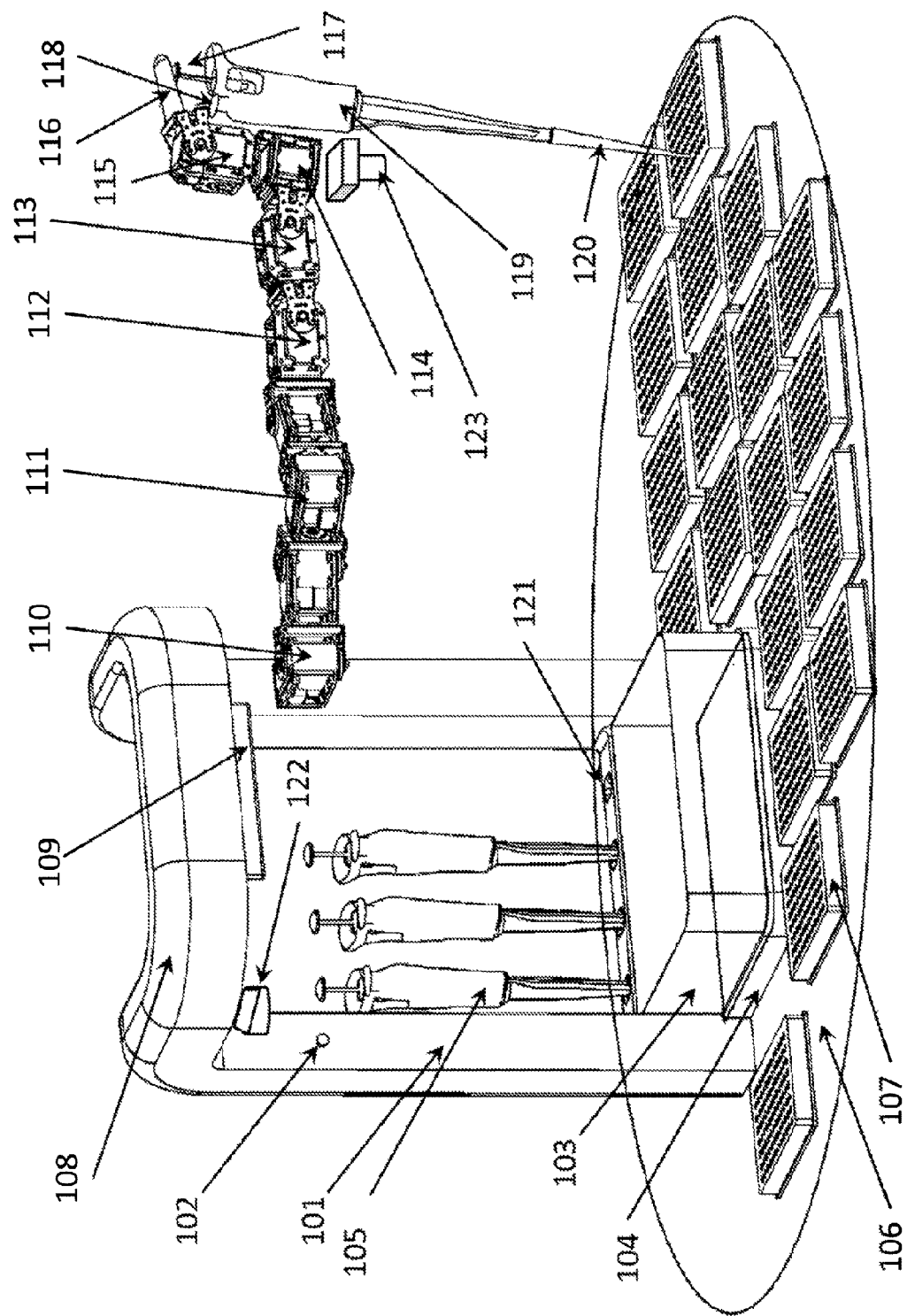
FIG. 1 is a three-dimensional drawing illustrating a liquid handling android.

A possible liquid handling android can be made as described in FIG. 1. The body 101 could be an injection moulded polymeric structure, either monolithic or in various parts, including active components (like electronics and cameras) and passive components like a weight ballast (solid or liquid-filled), preferably positioned in the lower part 104. In some embodiments, the body could include a foot (not shown) meant to provide additional stability. In other embodiments the body could be positioned onto a laboratory bench but, by hosting batteries and interfaces, could also be designed to be used in other environments, like in the field or in portable implementations. In the figure, the body hosts a ballast 104, a receptacle for a removable tip tray 103, a body camera in location 102 with the purpose of volumetric setting and possibly with the purpose of deck area monitoring and inspection for intrusion detection, a plurality of pipette slots 121, in the form of receptacles or hanging fixtures or magnetic holders or similar designed to host pipettes like the one indicated by 105. The body can include a lifting handle like the one described in 108, and mechanical elements like the one indicated in 109 making the interaction with the pipette easier, for example by allowing an easy access the ejection button for the tip. The body can include a twister 122, defined as the actuator capable of setting the pipette volume. Typically, this operation is performed by twisting the knob of the pipette, but it could also be achieved by electronic means for electronic pipettes—for example remote Bluetooth communication or physical electrical links. It should be noted that additional electronics accessories could improve the advantages of the system: for example, a temperature or pressure or humidity sensor, possibly connected to a USB hub and read directly from the software interface, could allow improving the calibration of the pipettes by integrating and correcting for this information.

The deck area 106 defines the operating surface of the liquid handling android, being larger, smaller or equal than the operating range of the arm. The deck area could have a circular shape, a rectangular shape or similar. Preferably the deck has a shape making intuitive to the user the correct orientation. The deck could be a virtual region, for example delimited by simple illumination, but also a soft pad (for example, a silicon pad that can be easily rolled above itself to reduce its size and recover a flat conformal shape when positioned onto a bench), or a rigid metallic or polymeric plate, including wood or composite materials. It is important to emphasize the possible advantages of virtual or foldable decks, since portability of a liquid handling android constitutes a main advantage for service and support operations, making the shipment of the android more effective cost-wise. In addition, a foldable or virtual deck allows saving space when the android is not in use. The deck could contain a plurality of locations providing specific information, either to the user either to the system itself. For example, labels, warnings, instructions, precautions, and disclaimers addressed to the user, but also localization marks, barcodes, coded symbols, tags, fiducial spots, to improve the space localization of the pipette and the consumables by means of the cameras. A plurality of types of consumables, for example the microplates indicated as 107, can be positioned onto the deck, either in a free format configuration, either in fixed or almost fixed format configuration. A fixed format configuration implies to precisely localize the consumable in a given position, without leaving an arbitrary choice for its orientation, while an almost fixed format configuration indicates an approximate region for the consumable, but leaving the option of rotations and displacements in proximity of the nominal position for the same. Fixed format configurations may profit from slots, rails or similar solutions. In all configurations, the presence of serigraphic or printed graphics can facilitate the user job of positioning a plate, but also simplifying the function of consumable localization by the cameras and providing a sense of order to the user perception, making the repetition of the same protocol an easier task. Optionally, the printed graphics and information could be performed in different colours, making the camera more selective to identify a part of the information hereby present.

The arm, in this case defined as the structure between element 110 and element 113, comprises a plurality of actuators or solutions with a similar functionality (for example, a cable driven system where the motors are actually localized outside the arm, or a pneumatic system using cylinders as actuators). In the present embodiment, actuators are chosen from the category of servo motors integrating gear reduction and angular feedback, allowing setting the actuator to a given angle between its body and the output axis. In a single unit, for example unit 110, the provision of power and serial communication link (for example based on the RS232, RS485 or USB standards) allows to input and output different information: examples of input are the desired position, the velocity profile for a movement, the maximum torque, the angular acceptance window; examples of output are the current position, the current velocity, the unit temperature, the unit status, and possible faults. The motion of the arm occurs mainly in the horizontal plane, being typical biochemical operations performed on a planar and horizontal bench with consumables which have a marginally different height. However, the insertion of tips and the aspiration and dispensing of liquids, for example, also require vertical movements. In this specific embodiment, the arm operates mostly in the horizontal plane and it has a more limited excursion in the vertical plane. One way to achieve the required displacement, for example, would be relying on two angular actuators setting the position in the horizontal plane and a vertical linear actuator. In alternative, the weight and complexity of the linear actuator could suggest its replacement by two angular movements, for example the angular actuators 112 and 113, allowing moving the pipette up and down by conserving its orientation in space through simultaneous movement. This feature can be important in consideration of the fact that the pipette verticality constitutes an important requirement for better volumetric performances of pipettes. For other reasons, it could be preferable to increase the number of angular actuators for a movement in the horizontal plane. For example, in some embodiments it could be desirable to define the orientation of the vertical pipette with respect to azimuthal rotations: this automatically implies at least three actuators for horizontal movements. The presence of obstacles or fixed structure could also require a larger number of actuators, for example four as depicted in FIG. 1. The choice of the arm configuration could follow good engineering practice and common sense, in view of the application and of the angular actuators performances.

The hand design could exploit concepts and components similar to those applied to the arm. In the depicted embodiment, the hand starts from actuator 114, which is actually the actuator taking care of the grabbing of the pipette. The grabber, not shown for clarity, can be a simple claw mechanism capable of exercising a pressure on the two sides of the pipette. It could also be a single claw mechanism, where the moving claw is opposite to a fixed claw which is conformal to the pipette. Claws can have, in general, a conformal shape, a planar shape, or a limited number of contact points with the pipette. Different design have different advantages: depending on the embodiment, the liquid handling android could be designed to deal with a single type of pipette, or with a multiplicity of models. It is obvious to those skilled in the art that claws have to be conceived accordingly, and their conception could be different for different pipettes. The hand may further comprise a camera 123, to be oriented and moved in different directions, independently or dependently together with the pipette, with the purpose of identifying the consumable and its position in space but also the position of the tip 120 or the pipette 119 once it has been grabbed from the body slot 121. It is important to realize that it is challenging to image, with a fixed camera, a typical deck surface characteristic of a biological or chemical test without going too far away from the deck. Therefore, the suggested embodiment indicates a solution for the problem by imaging the deck area by a series of pictures individually covering a part of the useful surface. The image could be recomposed in a mosaic by suitable software, allowing having a synoptic view of the deck space and the consumable thereby contained. The composite imaging could also allow—by tilting or translation of the camera or of the hand—to have multiple images of the same deck or part of it. This feature could be easily exploited with the purpose of obtaining stereoscopic information in order to reconstruct at least part of the three-dimensional information. This feature is particularly relevant in order to extract information on the height of the consumable, possibly required for the correct setting of the pipette aspirating and dispensing position. Three-dimensional information could also be achieved by means of using the focus information from the camera, provided that the camera has an adjustable focus and the optical configuration has a limited depth of focus. This method, would allow extracting depth information by simple scan of the object itself, and analysis of the spatial contrast of the image. A colour camera could also provide additional information, for example allowing identifying consumables and pipettes or other accessories based on the colour space distribution. The hand may include a thumb actuator 115, whose purpose is to actuate the thumb 116 with functionality similar to the human thumb in the manipulation of a pipette. The thumb movement could be a simple partial rotation around the axis, but it is important to notice that improving the precision of the thumb action, for example in its speed, position, and pressure sensitivity with respect to a human thumb, could introduce various improvements in the pipette manipulation: for example, improved mixing of liquids by rapid aspiration/dispensing sequences through the excursion of knob 117, improvements in the precision of dispensing by a reproducible position displacement or velocity profile, and an improved detection of the pipette stop by pressure feedback mechanisms. Ultimately, the thumb action could also depend on the liquid properties—making the pipette working in optimal conditions with viscous liquids or heterogeneous samples. As another example, a fast and reproducible thumb action could improve the performances and the reliability for on-the-fly dispensing of liquids, defined as dispensing of liquids without physical contact with the recipient-contained liquid. This possibility would enable performances that are not possible to be achieved by manual pipetting operations, with significant savings in time and in the use of tips. A combination of a multiplicity of dispensing and aspirating methods, combined with the possibility of individually calibrate them for arbitrary liquids (as described in a following section) supports the evidence that a liquid handling android can outperform easily a manual operator, both in capacity and quality.

Figure 6:
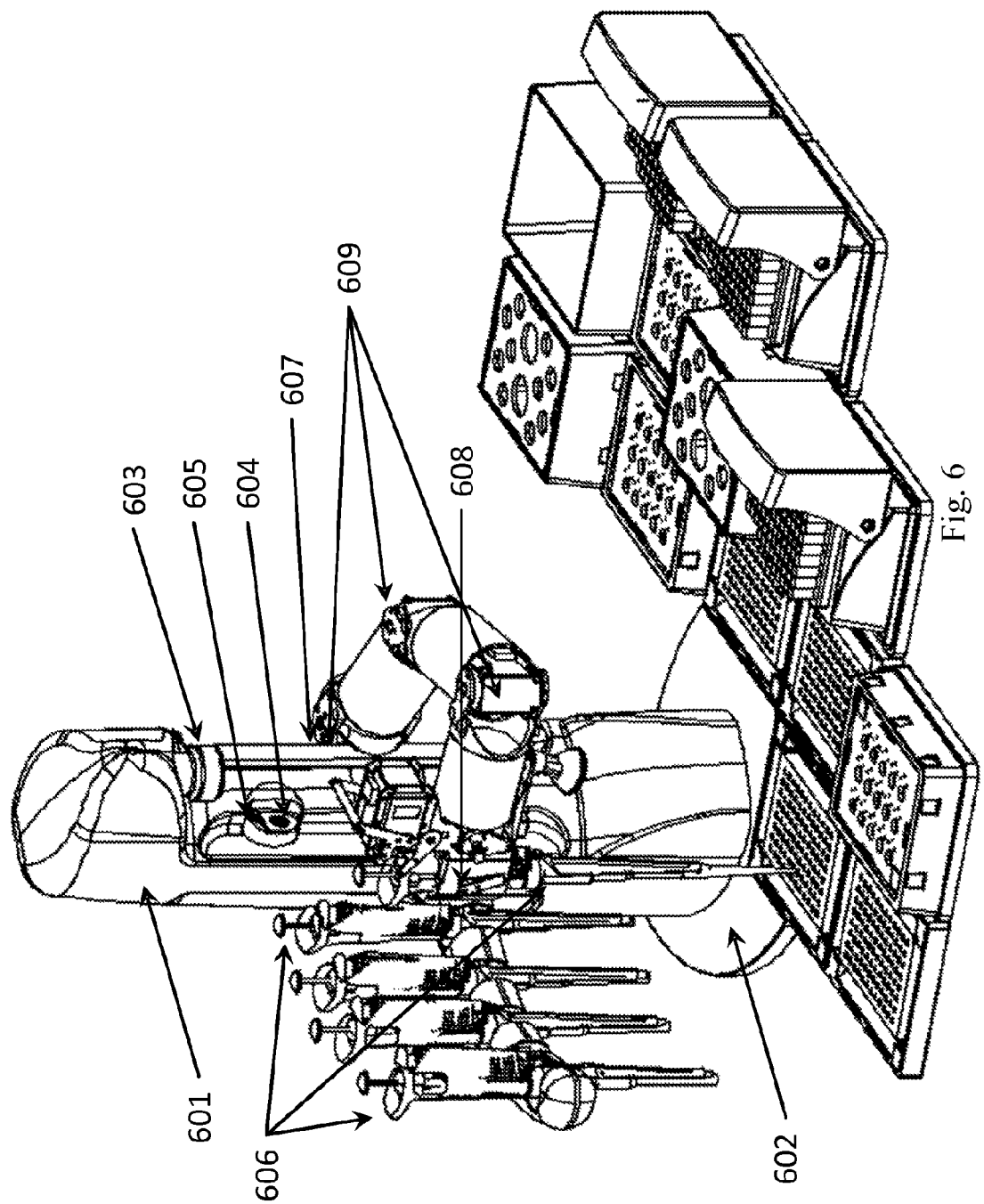
FIG. 6 is a three-dimensional drawing illustrating a second embodiment of a liquid handling android.

A second embodiment of a liquid handling android is described in FIG. 6. A plastic enclose 601 constitutes and contains the main body, which is designed as a vertical structure mounted onto a baseplate 602. The baseplate 602 has the purpose of providing stability to the system, and to make the system independent from possible vibrations and oscillations of the supporting bench—whether induced by the android itself or by external agents. The body 601 also include a rotating actuator 603 for the execution of the volume setting procedure. The rotating actuator is assisted by a camera 604 that, by means of the internal illuminator 605, is capable if imaging the digital counter positioned onto the pipettes 606. In this embodiment, the body 601 contains electronics and mechanics: in fact, the vertical movement of the arm is achieved by a linear actuator (not visible in the picture) that raises vertically the shoulder 607, allowing for the required vertical excursion of the arm. As a consequence of this, the arm functionality is limited to the displacement of the hand 608 in the horizontal plane, being the vertical movements achieved inside the body 601. Differently from FIG. 1, the arm therefore contains only three servomotors 609 that allow for complete coverage of the intended area.

Figure 7:
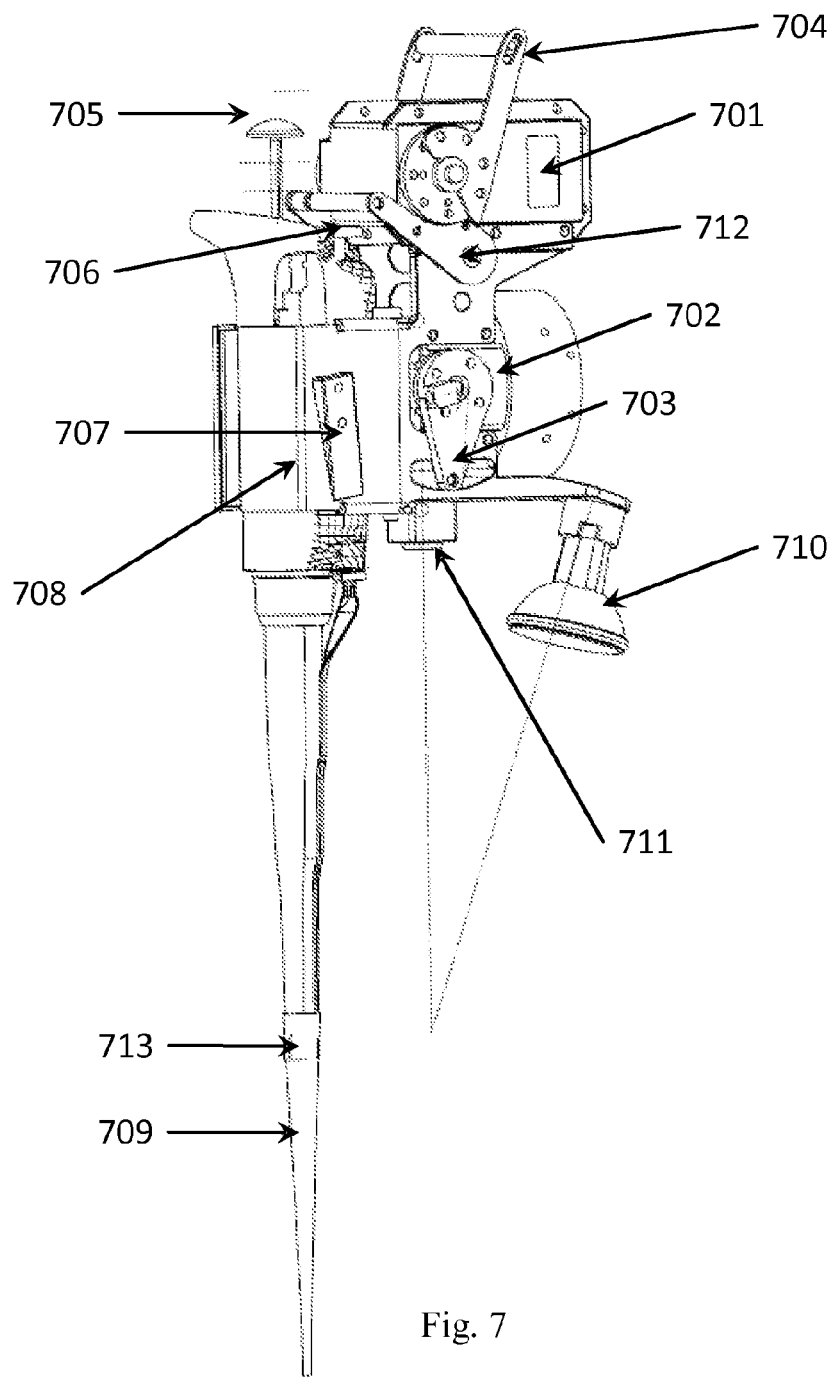
FIG. 7 is a three-dimensional drawing describing the details of a hand which is capable to grab a pipette, actuate aspiration and dispensing, and eject a tip.

Details about the hand embodiment are shown in FIG. 7. Two servomotors 701 and 702 assist the hand in manipulating the pipette, including grabbing, ejecting the tip, and actuating the pipette knob 705 for aspiration and dispensing of liquids. Servomotor 701 has the double function of applying the required pressure on the pipette knob 705, including the monitoring of the pressure feedback and the monitoring of the knob position in order to determine the pipette stop. The double functionality is achieved by means of cams, where cam 704 is always moving together with the servomotor 701 axis, while the cam 712 is actuated by the cam 704 only within a limited angular range. The pressure of cam 704 onto cam 712 actuates the button 706 on the pipette, inducing the ejection of tip 709 from the pipette. Another cam is actuated by servomotor 702: cam 703 actuates a lever (not shown) that slides on wedge 707, which in its turn pushes the clamp 708 against the pipette body and results in the pipette grabbing. A symmetric mechanism is present on the other side of the pipette, resulting in a symmetric clamping force aligning the axis of the pipette with the axis of the hand.

Importantly, the hand hosts a camera 711 and an associated light source 710. The purpose of the light is to apply uniform and constant illumination in the field of view of camera 711, field of view comprising the bird flight view of the deck, the imaging of the tip 709 and in this case also of the pipette end 713. Having these elements within the field of view, allows measuring the relative position of these objects within the camera image. In fact, the correction of the optical distortion of the lens allows determining the radial line—passing through the objective of camera 711—along which an object within the field of view lies. Therefore, its transversal position can be reconstructed by estimating its vertical location. The vertical location of an element, for example the tip end, can be estimated in different ways: by means of the lens focus, by contact of the same object against a reference of known vertical position (sensed through the pressure feedback of the vertical motion), by multiple displaced images of an object which is not connected to the hand, by stereoscopic imaging of two cameras are mounted on the hand, by measurement of the apparent size of a 2-dimensional barcode of known dimensions, and other methods.

Detailed Description of Volumetric Setting

Figure 2:
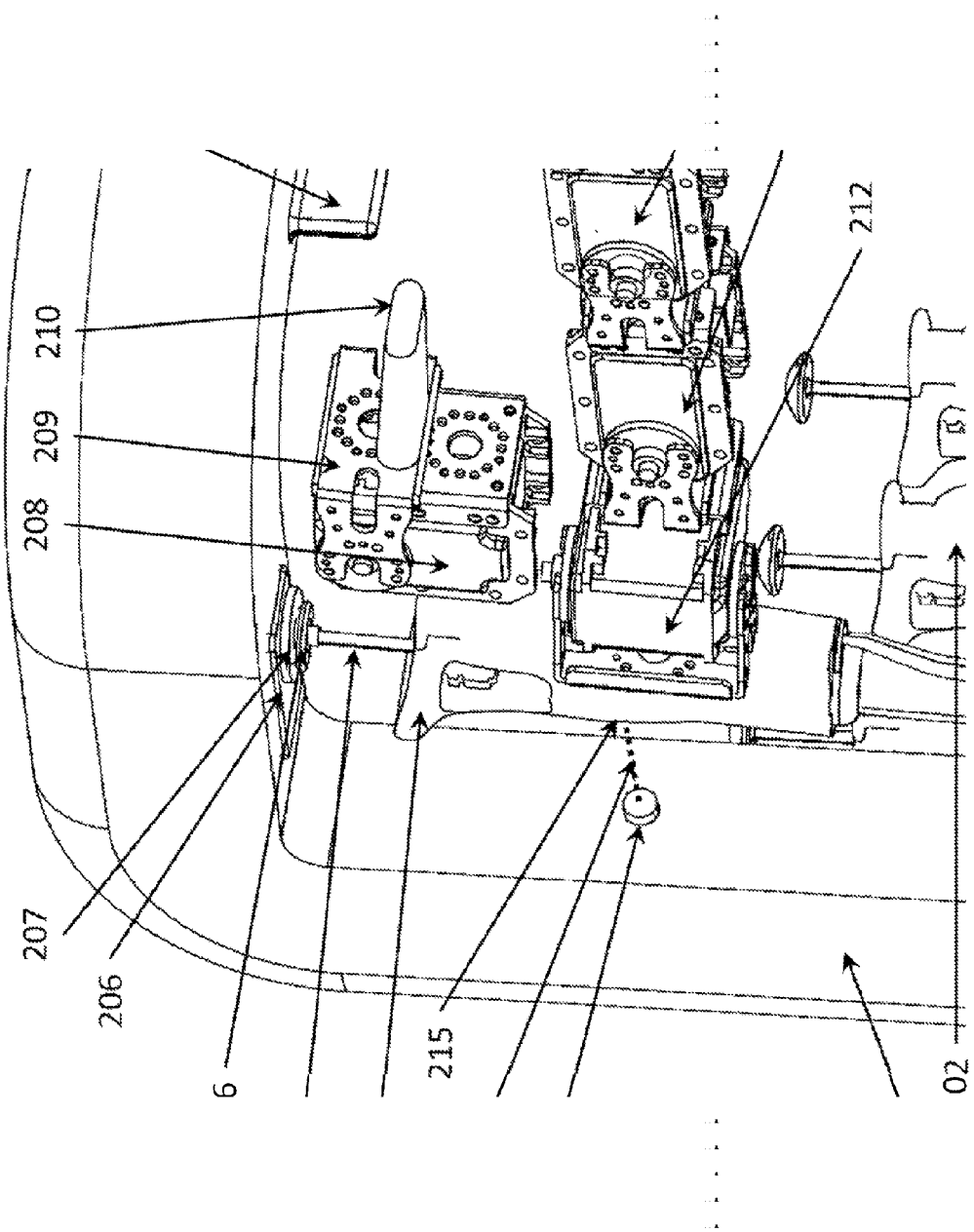
FIG. 2 illustrates the details of setting the desired volume of a pipette by means of vision-based feedback.

A possible embodiment describing methods and devices for the definition of the pre-set volume in an adjustable pipette is described in FIG. 2. In the picture, a camera 203 is located inside the body 201, body already described in FIG. 1. The camera is positioned in such a way to be able to image the pipette display 215 (not directly visible in the picture being covered by the pipette body but indicated for example in location 313 of FIG. 3) indicating the dispensing/aspirating volume of pipette 204. Obviously, the arm which is partially visible (actuators 213 and 214) has been suitably designed in order to allow this position to be reached. The camera could either image the display from the front, or from a certain angle in whatever direction and plane (for example, from the top or from the bottom, from the left or from the right). The camera could be assisted by artificial illumination, either from the environment or from sources contained in the liquid handling android, either from natural sources. It is useful to combine the display monitoring with the capability of adjusting the pipette volume setting. This is accomplished by the actuator 206 connected to the knob twister 207. The actuator can be set either by its angular position, either by its angular velocity. The knob twister is an element, preferably of elastic material, which has been designed in order to be able, by simple pressure of the knob against the twister, of applying a torque on the knob therefore allowing—as done for the majority of pipette types—to perform the required pipette adjustment. In some embodiments, the twister could be a rubber based cylinder with a concave (truncated) cone carved into its body: the cone shape would allow to conformally adjusting to different sizes of pipette knobs.

Detailed Description of Tip Ejection

Figure 3:
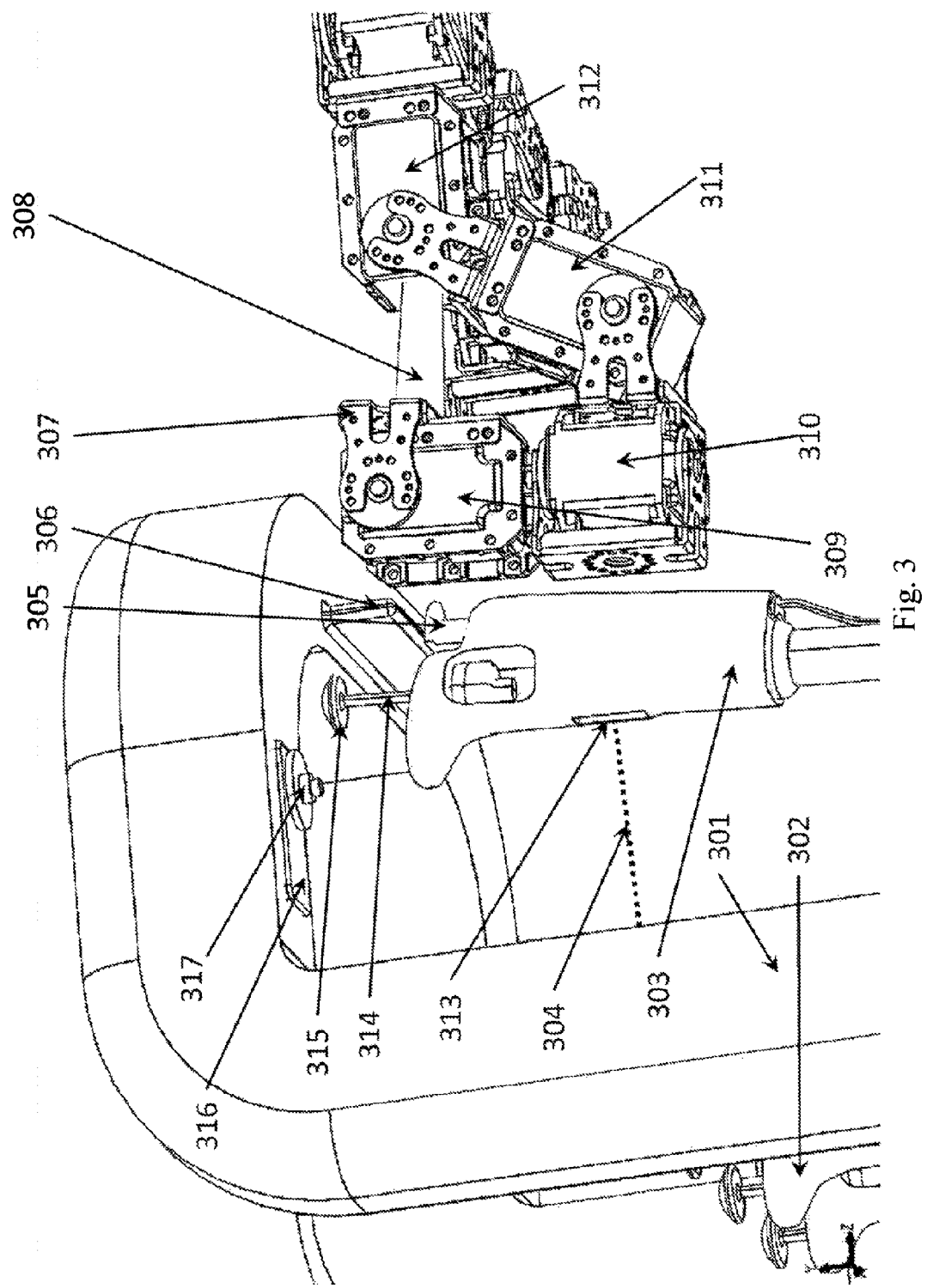
FIG. 3 illustrates the method of ejecting a tip by means of a fixed fixture and movement of the pipette itself.

A possible embodiment describing apparatus and methods for the action of tip ejection is shown in FIG. 3. Obviously, tip ejection in a liquid handling android is complemented by tip insertion onto the pipette. However, in most of the present pipettes the tip insertion is simply performed by applying a certain pressure when the pipette body has been inserted into the tip. Clearly, this operation is feasible in an embodiment as described in FIG. 1. Concerning the tip ejection, multiple solutions could be exploited, including the direct action of the ejection button by means of a dedicated actuator most probably located into the hand of the liquid android. However, there is an economical solution which doesn't require an additional actuator, as shown in FIG. 3 for the liquid handling android embodiment already described in FIG. 1. The arm allows localizing the pipette 303 in a configuration where the ejection button 305 of the same pipette is facing a fixed structure 306, for example fixed with respect to the body structure 301. The actuation of the ejection button is achieved by a force generated by the arm itself, for example by the action of the actuators 309 and 310 in order to have the fixed structure 306 and the ejection button 305 being pushed one against the other. This solution allows saving at least one actuator and a certain complexity in the hand, resulting in a lighter and more reliable solution. An appropriate choice of the shape of the structure 306 allows also ejecting the tip in different spatial position, something which is desirable to avoid the accumulation of tips into a limited area of the waste tray 103 shown in FIG. 1.

Detailed Description of Volumetric Monitoring

Figure 4:
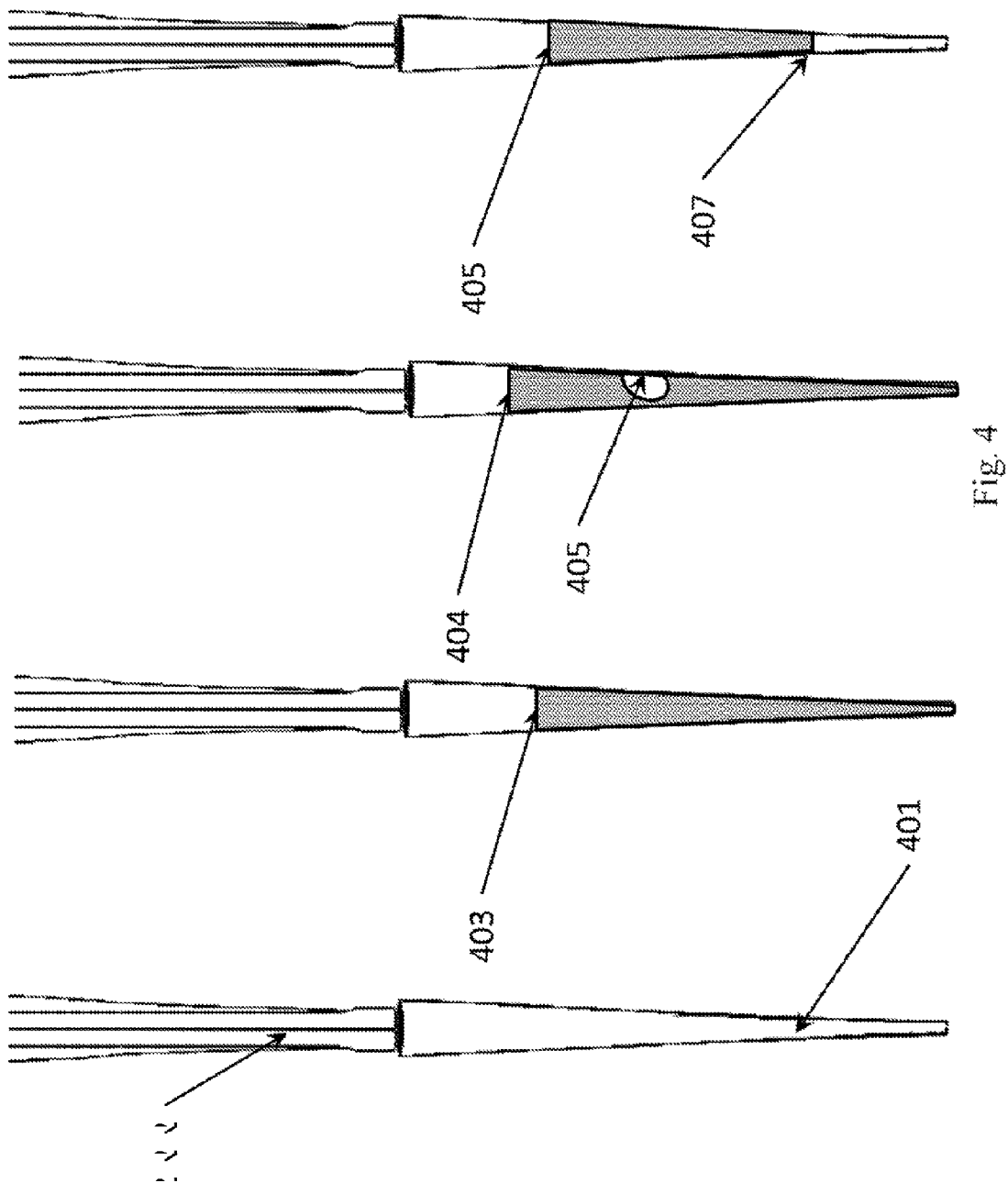
FIG. 4 illustrates the details of vision-based tracking of the liquid volume being used.

A possible embodiment of methods and devices achieving volumetric monitoring and traceability of pipetting operations is shown in FIG. 4. The four images correspond to four different snapshots taken by a camera, which in the liquid handling android previously described could either be camera 123 or camera 102 of FIG. 1. For simplicity of description, the image is taken from a position which is orthogonal to the pipette axis: however, this is not strictly required and most angles of view are possible. The image can visualize in part or in full the pipette body 402 and the tip 401. As it is visible in the leftmost image, a reference image of an empty pipette constitutes the reference and it could also be stored—temporarily or permanently. It is understood that the image could be taken in a reference position of the arm, so providing a uniform and constant background information and illumination.

In the second picture from the left of FIG. 4, it is depicted a tip which has been loaded by a given amount of liquid, according to the volumetric settings of the adjustable pipette. It is obvious to those skilled in the art that every set volume corresponds, for a given tip, to a given location of liquid meniscus 403. In this respect, therefore, the meniscus location constitutes an indicator that the pipette has aspirated correctly the desired amount of liquid.

Conversely, the reference image constitutes the logical reference after a dispensing operation, where the presence of droplets or liquid left-overs can also be detected in a similar way. In the third picture from the left in FIG. 4, it is shown a pathological case where the aspiration is not occurred correctly. Visibly, a bubble of air 405 has been introduced in the pipette, modifying the actual liquid volume contained in the pipette with respect to the desired volume. According to the origin of the bubble, the meniscus 404 could be at the correct position (defined according to the considerations done for the second picture from the left of the same figure), therefore indicating that the actual liquid volume in the tip is lower than expected. The liquid meniscus could also be at a higher level, indicating for example that the bubble has been formed after aspiration, or could even be lower than expected—suggesting a serious problem in the liquid collection. A simple and practical case occurring in laboratory practice is shown in the rightmost picture of FIG. 4: a lack of liquid in the container where the pipette has aspirated the liquid, or the incorrect position of the tip with respect to the liquid level, has resulted in a partial aspiration of the liquid at the advantage of air contained in the pipette. The meniscus 405 is most probably in the correct position; however a second liquid-air interface is visible in location 407. All these undesirable behaviours can be made available to the user, significantly improving the interpretation of the data generated by the assay. In all cases, the image contains significant information that would be lost in manual operations. This useful information could either be processed online, in order to try recovering the process, either simply stored offline for operator monitoring and quality control purposes. Overall, a similar imaging configuration could be used for controlling the position of a tip in a consumable with respect to the liquid level. The imaging of the consumable, and the identification of the liquid level, could allow determining the vertical distance between the liquid and the tip, allowing precise sipping or dispensing of liquids. Similarly, the same procedure could be applied to aspirate liquid in particular vertical location of the liquid, for example in the case of separated blood and aspiration of buffy coat at the interface between plasma/serum and erythrocytes.

Detailed Description of Vision Assisted Tip Positioning

Figure 5:
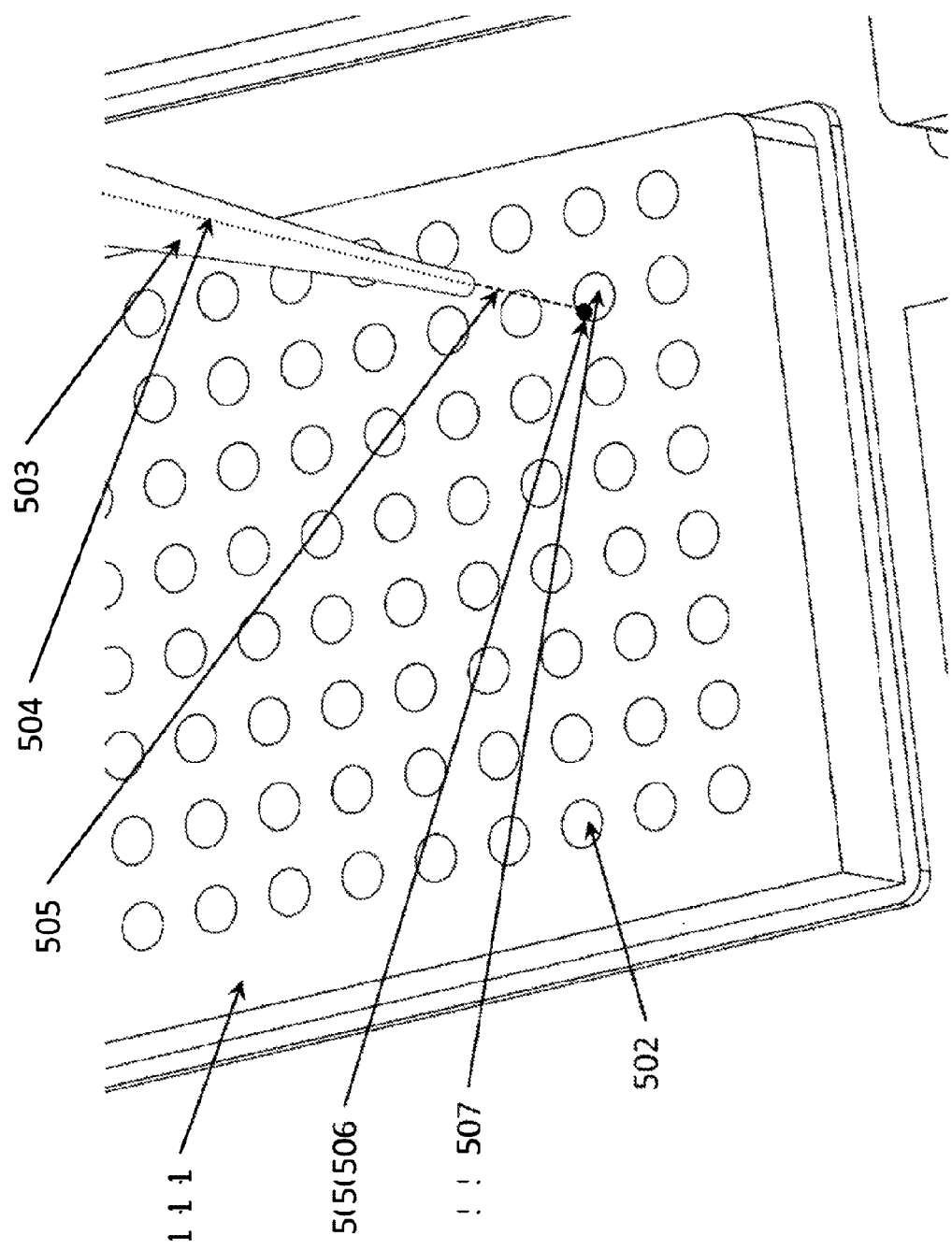
FIG. 5 illustrates the detail of vision-based relative positioning of the pipette tip with respect to other consumables.

A possible embodiment describing methods and apparatus for achieving vision assisted positioning of a tip is shown in FIG. 5. The image corresponds to the image taken by a camera which is preferably connected to the pipette hand, for example camera 123 described in FIG. 1. If the camera is connected to the pipette hand, grabbing the pipette 119 connected to tip 120 in FIG. 1 will result in a reproducible and constant position of the pipette tip 504 visible in FIG. 5. Therefore, this information constitutes already an important control on the proper grabbing of the pipette from the hand. It is understood that different pipettes and different tips could result in different images and shapes, so the tip imaging also represents a possible method for making sure that no mis-identification has occurred. Additionally, the image may contain—as in the case of FIG. 5—additional objects within the field of view. It is well known in the art that any object could be either in focus, either out of focus, accordingly to the type of optics and sensor utilized, and obviously their distance from the camera. The arm capability is such that it is possible to operate the arm at a desired height, which of course means that the distance between the consumable and the tip will be set to a desired value. In this conditions, it is possible to identify the lateral alignment of tip 504 with respect to the desired well position 507 according to the following method: the axis 504 of the tip 503, when prolonged, will identify the trajectory that the tip will perform for a vertical movement (in the example that the tip is vertical, as it should typically be). However, a given and typical distance of the tip with respect to the consumable will define a single point in the image that the tip will intersect when localized at the same height of the identified well. Therefore, the relative horizontal alignment of the tip can be achieved by imaging the same tip within the field of view, and applying an offset in the imaging plane: this point should be directly positioned onto the desired destination, by applying lateral movements of the arm without changing the distance of the tip from the consumable. It should be remarked that this method works also in presence of optical distortions, that can be corrected either in full by vision analysis method either by empirical alignment.

In another implementation, as visible for example in FIG. 7, the camera can image the tip while the tip is approaching the liquid surface. With respect to an image where the tip is far away from the liquid, an image where the tip is in contact with the liquid will change the image of the tip, and therefore such change can be used to identify the position where the tip touches the liquid surface, for example with the purpose of aspirating or dispensing nearby the liquid surface.

The difference in the images can be enhanced by suitable illumination of the tip or of the liquid: as soon as they come in contact, the refraction index of the tip polymer and the refraction index of a liquid are similar, and therefore light will channel through the other medium under the guidance of internal reflection along the materials surface. The change in the illumination configuration can be easily identified and lead to the detection of the tip-liquid contact. Illumination conditions particularly suited to the internal reflection exploitation can be achieved by means of light emitting diodes or lasers, or under the guidance of light guides, like for example optical fibres.

Detailed Description of the Domino Deck

Figure 8:
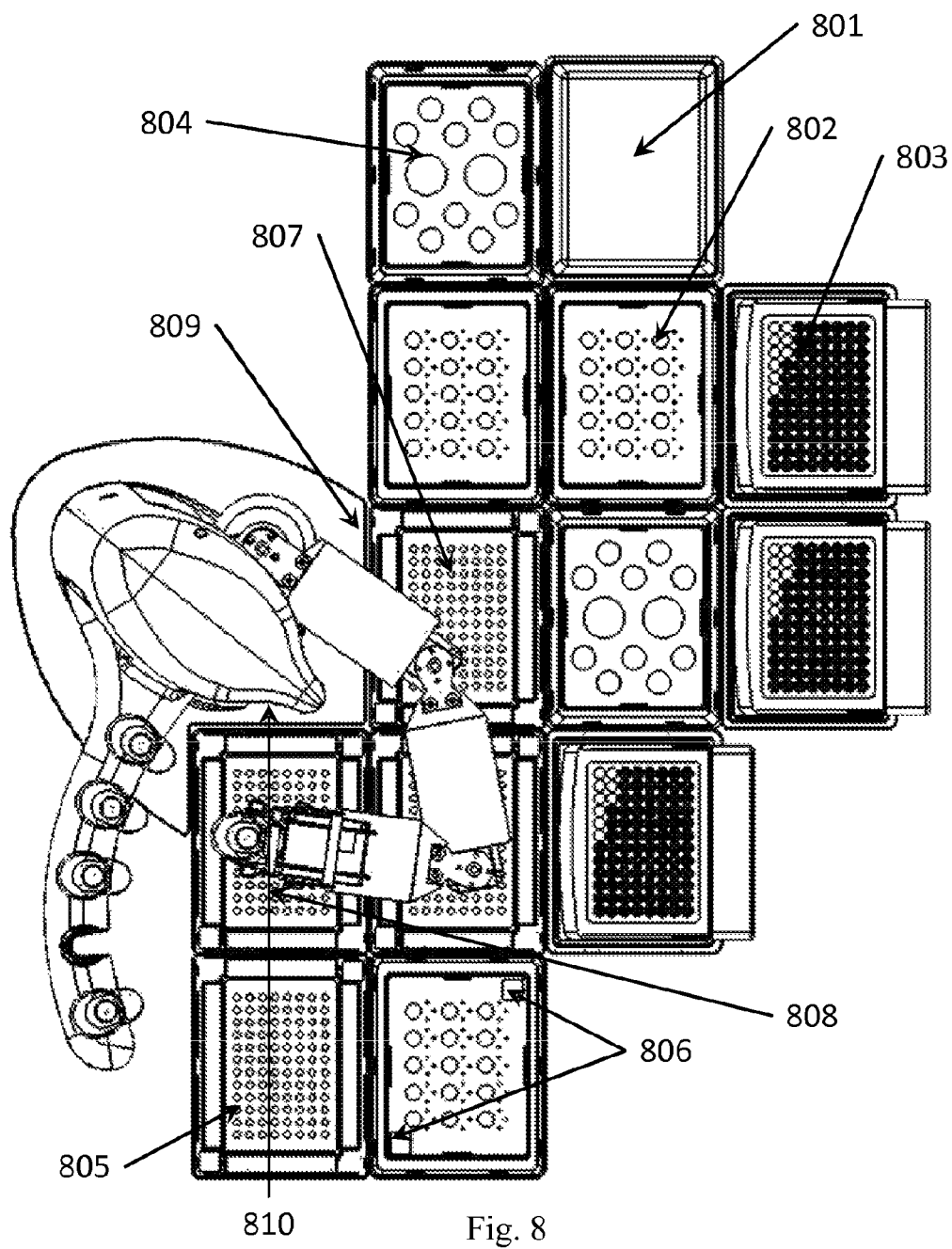
FIG. 8 illustrates the structure and composition of a domino deck based on domino blocks.

A possible embodiment of a deck configuration is shown in FIG. 8. Differently from the deck described in FIG. 1, the consumables are organized in a geometrical manner by means of holders called blocks, defined as reusable or non-reusable supports capable of holding one or a plurality of consumables. A feature of the blocks is the possibility of assembling them into a larger structure called mosaic, which is a planar composition of blocks organized according to some pre-defined rules but with a certain pre-defined flexibility. In FIG. 8, different types of blocks are assembled together: for example, block 801 is intended for the collection of used tips, bock 802 is designed to contain and support different types of microtubes, block 803 is intended to hold and support tip racks, block 804 serves the support of larger tubes like for example 15 mL, 50 mL and blood tubes, and block 805 contains a microplate. These blocks are not exhaustively covering all possibilities. For example, a block could be designed to host simultaneously pre-loaded reagents, specific consumables like tips, barcodes for processing information, tubes and empty consumables for allowing the users providing their own samples. In this last configuration, it is possible to conceive a domino block as a single unit that doesn't require external blocks for processing, making therefore the domino deck a collection of independent experiments that do not depend from each other. Importantly, domino blocks can be complemented by information by means of NFC, RFIDs, linear barcodes, optical recognition marks and two-dimensional barcodes as indicated in 806. The purpose of providing additional information reliefs the system in active and contact-less identification of the blocks, for example by means of the camera 711 described in FIG. 7. Other ways of extracting the domino block information is by means of electrical contacts positioned on their sides and coming into contact with neighbouring blocks, and propagated to the other blocks by means of an electrical network. One important feature of a domino deck consists in the capability of adapting its configuration to the user needs, while simultaneously being able to organize and rule the assembly of the blocks. In fact, the domino block could present keys on the sides, for example mechanical keys or magnetic keys, preventing the user from assembling the domino block incorrectly, and also validating the choice of a configuration by some forces keeping the assembly all together. One embodiment for a key is a mechanical configuration, similar to those implemented in LEGO toys for the purpose of education and play. Another mechanism consists in specific magnetic configuration: for example, along a side designed to be oriented in direction "down" the side could host a plurality of magnets presenting a suitable magnetic configuration. Poles in the configuration SNS (South-North-South) could be matched to sides presenting NSN (North-South-North) as a consequence of an attraction force, while sides NSN will be pushed away from a side NSN (similarly to the repulsion force of a SNS side when pushed against a SNS side). The advantage of a magnetic configuration consists in an attractive force validating an allowed configuration, while a repulsive force will prevent assembling blocks with the wrong orientation. These magnetic forces could also improve the overall organization of the domino deck by means of connecting to an external reference structure. For example, in FIG. 8 the block 807 is magnetically attached to the base below the body of the android by means of a SNS magnetic configuration facing a NSN magnetic configuration generated by magnets embedded on side 809. Similarly, block 808 is magnetically connected to magnets position on side 810 of the android base through an SNS magnetic configuration facing a NSN magnetic configuration. In this example, what prevent to rotate by 90 degrees the block is the different pitch between magnets, shorter on side 810 with respect to side 809. For the same reason, the blocks in the domino deck cannot be rotated by 180 degrees or by 90 degrees.

One important advantage of a Domino deck consists in an optimal space occupation of the laboratory bench, being external to the android body. In fact, the space occupied by the system is limited to the space required by a given experiment, contrarily to the configuration of today liquid handlers that occupy bench space irrespectively of the complexity of the experiment involved. Additionally, it allows minimizing the occupied bench space when the system is not used, for example by storing the domino blocks elsewhere or by assembling them in a vertical pile occupying the footprint of a single domino block. In general, users can exploit different domino blocks according to their typical experiment, by varying the amount of blocks of the various types which are required and without using the blocks which are unnecessary.

Detailed Description of the Space Localization of the Arm

Figure 9:
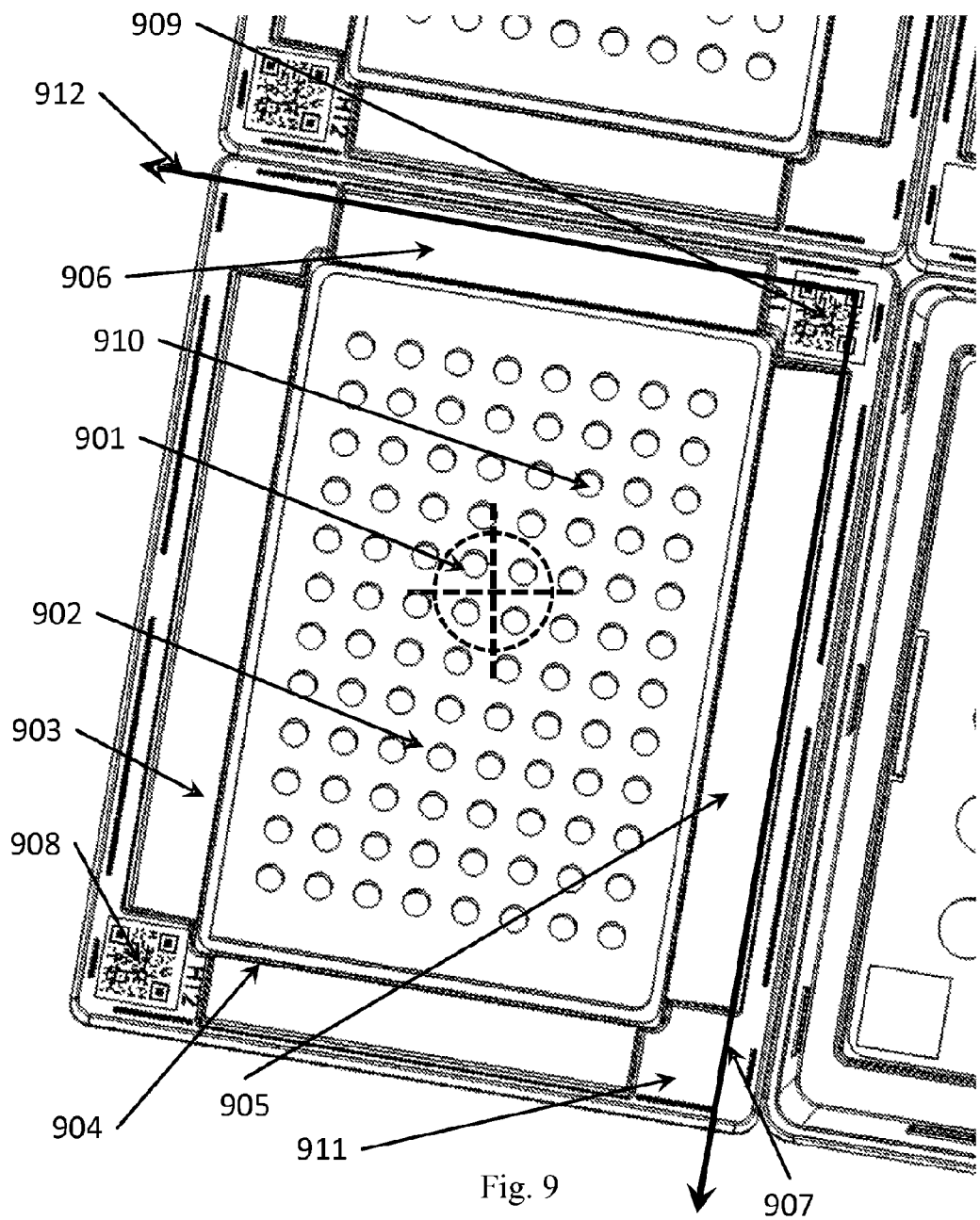
FIG. 9 illustrates one embodiment for the use of computer vision for the purpose of three-dimensional localization of the arm position.
Figure 10:
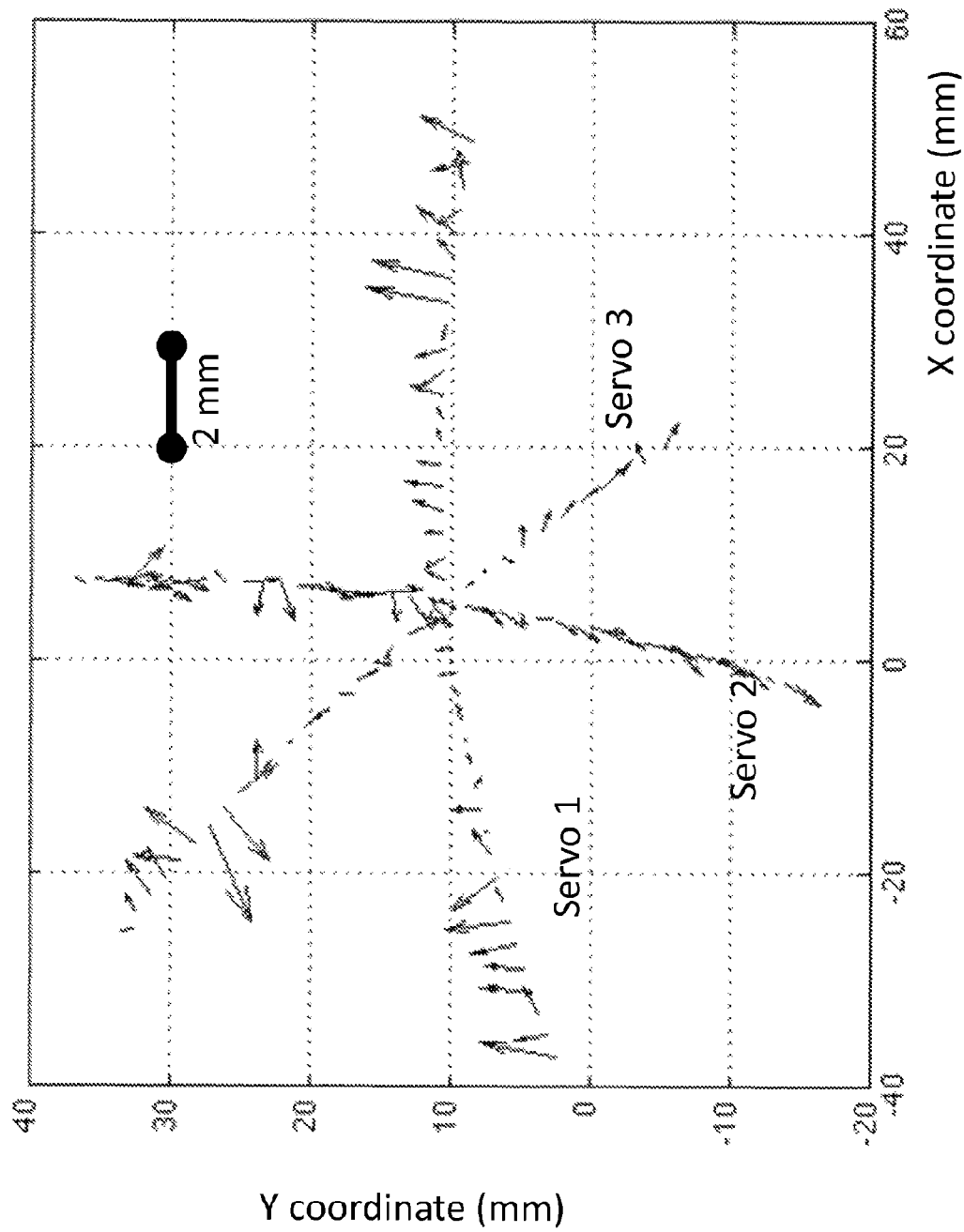
FIG. 10 illustrates the capability of three dimensional localization of the arm position and application of a method for improving the intrinsic spatial resolution of the system.

While multiple procedures and methods for positioning are known to those skilled in the art, including the use of precision mechanics and encoders and decoders of X-Y-Z Cartesian robots, we describe a method which is particularly suited for the identification and localization of consumables by means of a simple camera mounted on the moving arm. The camera and arm geometry here described is the one shown in FIG. 6, the arm 609 holding a pipette 608 by means of the grabber 708 shown in FIG. 7 together with camera 711 and related illumination 710. FIG. 9 represent a possible image taken by camera 711 while moving above a certain block, to be accessed precisely for the purpose of pipetting in one given position (for example well 910). It should be noted it is critical to extract the relative position of the pipette axis in three dimensions with respect to the desired pipetting location. Known the pipette tip length (for example by the pipette model or by other techniques including the sensing of the pipette tip contact, stereoscopic imaging, external measurement by means of camera 604 of FIG. 6, and other methods), and given the fact the pipette tip could be visible within the field of view of the camera (as possible in FIG. 7 for pipette 709 by exploiting a suitable objective for camera 711), it is evident that the lateral position of the pipette tip end with respect to the camera axis can be computed in the space of the image sensor coordinates (pixels) and converted in real space lateral displacement once the conversion scale is known for the plane where the pipette tip end resides. The conversion scale can be achieved in multiple ways, including the use of a two-dimensional barcode of known dimensions in the same plane. However, FIG. 9 shows that knowing the relative position of the pipette tip end with respect to the camera is a partial solution to the problem addressing the positioning of the pipette tip end into a well 910, since it is still required to move the camera axis (shown by the hatched cross 901) at a given offset (in the real space) with respect to the consumable 902.

The following method shows a procedure which has the advantage of being rapid and robust, being capable of compensating any misalignments and locally adjusted for each individual block or small area of the deck. In fact, block 911 is equipped with different features. One feature is the presence of mirrors 903, 904, 905, 906 positioned on planes which are at 45 degrees with respect to the horizontal plane, and reflecting in the upward direction the image from the side of the microplate. These mirrors allow the optical inspection of any user-labelled barcode put on the vertical sides of the microplates, that can be measured by the camera 711 easily irrespectively of the sides where the barcode is applied, and potentially detecting any microplate rotation if the user barcode should be in a given side of the microplate. The same barcode identification capability can be exploited to detect other barcodes implemented into the block 911 in positions 909 and 908 for example. It should be emphasized that the choice of two barcodes could be reduced to a single barcode and could be extended to a plurality of those, with the purpose of increasing the system robustness or the amount of information to be read by the camera. The two dimensional barcodes mounted in block 911 are positioned at about the same height of the wells, or at a known offset in the vertical plane. The reading of a barcode, for example of a QR barcode, also provides to the user information about its apparent size, which is the size measured by the camera in its space (typically, measured in pixels along the directions of the dimensions of the sensor). Having barcodes of known dimensions, or of dimensions which are reported into the content of the barcode itself, allows therefore to define the spatial conversion scale to convert any distance measured by the camera in the same plane into real dimensions. Alternatively, if the barcode is of unknown dimensions, two barcodes at a known distance can serve the same purpose, for example by knowing the distance between barcode 908 and barcode 909. Indeed, for the case of camera with unknown pixel shape the information about the barcode angle has to be used in order to extract the suitable conversion scale (different in the two directions of the image sensor). In summary, measuring the dimensions and the angle of a single two-dimensional barcode allows for measuring distances in the same plane of the barcode, or in its proximity. However, for a given camera and objective the conversion scale changes with the distance according to simple projective rules, once the camera images are corrected for the objective distortions. So, a vertical scan performed by moving vertically the camera at known steps (for example, knowing the gear factor and the steps of a motor moving the arm vertically, allows to construct a curve that automatically provides the user, by interpolation and extrapolation, the vertical distance for a given camera and objective from the barcode itself. Ultimately, the same curve can be used in a reverse manner to extract the actual distance of the camera from the barcode, and knowing the offset of the pipette tip end with respect to the camera: this inverse method allows solving the problem of vertical positioning of the pipette end tip with respect to well 910.

Similarly, the lateral offset of the camera axis 910 with respect to well 910 can be computed by knowing the lateral offset of well 910 with respect to a barcode 909 in the reference frame described by arrows 912 and 907. This offset is specific to each module, and can be stored into a suitable way externally or internally to the module (for example, by means of a database, inside the barcode data, or by an RFID or NFC tag). To achieve the target of relative positioning of the arm, it should be noted that the camera axis 901 is localized in the reference frame 912 and 907 by the measurement of the barcode angle, its position in the sensor image and the previously described spatial conversion scale: the transformation between the camera reference frame and the real space reference frame of the block become uniquely identified by a single image. So, putting all elements together, the present method allows precise relative positioning of a pipette with respect to a location in a given consumable by means of a camera mounted on a robotic arm, using the information provided by a barcode.

Figure 11:
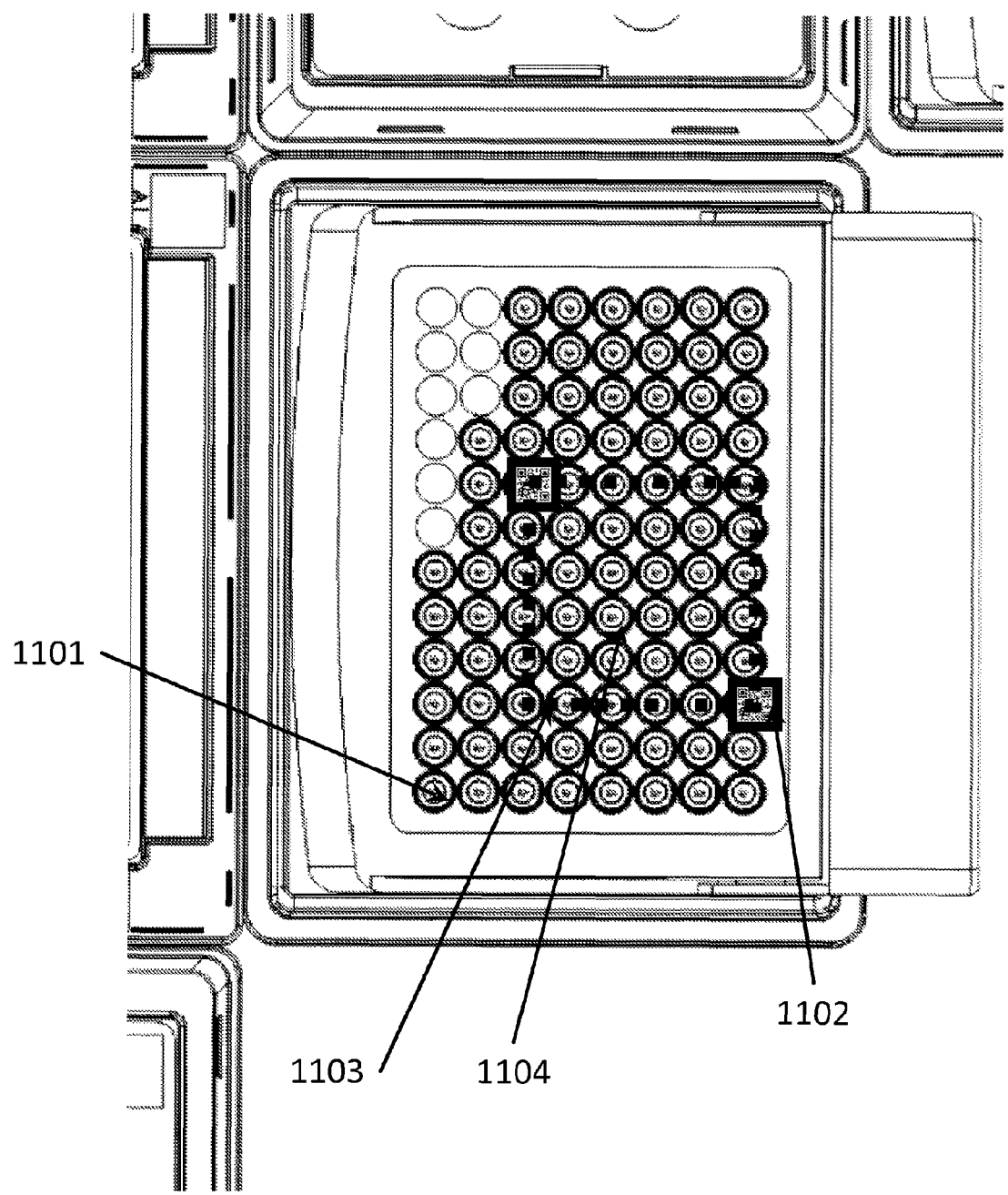
FIG. 11 illustrates one embodiment for the use of computer vision with the purpose of localizing the available tips in a tip rack.

In fact, the present method can be used also for precisely identify the parameters transforming the angles of the servomotors 609 of FIG. 6 into relative coordinates within one block. This approach has the advantage of precisely refine the mechanical precision in presence of the arm twisting, bending, imperfections in the angular determination, inaccurate arm sizes and dimensions, assembly inaccuracies and in general improving the reproducibility. In summary, the non-linear, non-invertible transformation of the servomotors angles into the camera position in the real space depends on a large number of external parameters, but is a known analytical function following basic trigonometric rules. However, many of these parameters are more accurate when computed locally, for example the bending of the arm could vary as a function of the arm configuration (its extension, for example). The method here disclosed is based on multiple images of block 911—similar to the image of FIG. 9—where the images are displaced by a known, local angular amount for any of the motors, allows creating a dataset of images where the barcode position and angle is measured within the camera image. Using the arguments explained before for a single image, the distances between the theoretical positions of the camera in the barcode reference frame 912 and 907 and the actual distances can be minimized by means of a least squares minimization algorithm, and therefore an optimal local transformation can be created and used afterwards. This procedure can be repeated rapidly over time, for example triggered by a large discrepancy between theoretical positions and actual positions during the arm operations, in order to maintain the system highly reproducible. In FIG. 11, an example of the residuals that can be obtained by changing individually the angular position of the three servomotors 609 shown in FIG. 6, for a number of angular settings (each of the intersecting lines corresponding to the modification of the angle of one individual motor, as indicated in the plot labels). The arrows in the plot indicate the residuals, defined as the deviation of the expected position vs. the actual position measured by the camera, after having applied the previously mentioned minimization procedure. The size of the arrows (magnified by a factor 5× in order to make them visible in the plot) indicates the error in positioning of the system. The method here described allowed improving the spatial precision of the system by a factor 6×, taking average residuals from 6 mm (mainly given by the precision of the mechanical system and of the electronics) to less than 1 mm.

Detailed Description of Tips Identification and Localization

A problem specific to liquid handling instrumentation is the need of identify, localize, count and dispose the liquid handling consumable called tip. There many different types of tips—and typical liquid handling operations imply the disposal of the tip after each liquid dispensing step, to avoid further contamination. The consequence is a complex logistics even for relatively simple protocols, both in manual operations and liquid handling performed by automated systems. In particular, pipette tips in some disciplines have also strict requirements in terms of sterilization and contamination before operations actually have place: the consequence is that a typical laboratory has a very complex tip management logistics, induced by multiple tip types, compatibility of each tips for each equipment and manufacturer, and of the formats and packaging associated to those. Essentially, all instrument manufacturers supply users with their own tip racks, tip rack being the name for a structure organizing tips in a regular array, and try to offer the widest choice possible in order to allow any operation on any instrument. Consequently, tips supply becomes an expensive activity both for users and instrument suppliers.

Hereby, we describe a novel solution allowing our androids to use any tip which is already being used in the laboratory. The solution is totally independent from the tip rack, e.g. the holder containing the tips. The solution allows also to identify uniquely the tips, and to know which tips are usable in a rack without the requirement (demanded by most instruments) to start operations with unused and new tip racks. In this way, evident economy can be achieved by the customer, simultaneously obtaining the maximum flexibility in using high quality consumables on the android.

The solution consists in identifying and localizing tips by means of top-view vision, for example the one achieved by means of camera 711 in picture 7. Any tip rack can be positioned in a domino block like the one shown in FIG. 11, the domino block essentially being a simple box (possibly with a surface with an anti-slip pad to avoid undesired movement over time of the tip rack itself) capable of hosting the vast majority of tip racks commercially available. It is very common to purchase tip racks that organize the tip consumables in the same geometrical configuration of microplate wells, e.g. a rectangular array of 12×8 tips which are spaced apart by 9 mm. Assuming this configuration, in order to be able to use tips effectively we need to deal with various aspects: the identification of the type of tips, the identification of the available tips, the determination of the height of the tip upper part that will come in contact with the pipette end. Even if these operations could be performed by direct image processing, e.g. vision-based algorithms identifying shapes and structures, it would be hard to be robust enough to be able to deal with hundreds of different configurations and designs which are not known a-priori.

Our vision-based solution consists in inserting into the tip racks two buttons 1101 and 1102. The buttons could be either inserted by the user before executing an experiment, but also before autoclaving the tips for further reuse, or at manufacturing. The two buttons could be made in different ways: as a simple cork to be inserted into a tip of the corresponding type, or as a passive stub similar to the upper part of a tip and having about the same external diameter. Buttons would require a barcode or similar optical mark at the top, the barcode being an easy and robust solution for identification and localization by the top-vision camera mounted on the arm. The advantage in using two-dimensional barcode consist in the fact that they will automatically provide the precise vertical position of the tip for grabbing, and also the correct transversal scale for identifying the conversion scale in the image allowing to reconstruct spatial dimensions. Spatial coordinates are needed both for guiding the movement of the arm in order to grab a tip, but also to compute and determine the number of available tips, and their localization. In fact, barcodes 1101 and 1102 would be used to define the region of the tip rack where tips are present. In the example from FIG. 11, all the 34 tips localized in the matrix defined by the two buttons as corners would become a region from which the arm will pick the tips, region highlighted in the picture by means of the dashed rectangular perimeter 1103. It is evident by anybody skilled in the art that the suitable choice of the corners would allow choosing the region of the tip rack to use, and allow counting (by means of the known pitch among tips) the number of tips available. Similarly, the content of the barcode would provide to the system the information on the type of tips being hosted in the specific rack. The method here described by means of two barcodes, can be easily extended to a plurality of barcodes and different methods for indicating the usable sector of the rack for tips extraction. This method therefore provides the way of localize, identify and count tips in a substantially generic tip rack, and the same principle could be used for the extraction of partial information—for example in combination with tip recognition methods to discover possible holes in the tips formatting (as an hypothesis, one tip being absent in location 1104).

It should be noted that the same method can be applied to different types of consumables that imply picking operations: for example, needles for the purpose of liquid handling could be considered under the same methodology, with equivalent advantages.

Detailed Description of the Software Interface

An important element of the liquid handling android is constituted by the software interface, a generic name including the package communicating with the camera, actuators and electronics, controlling and synchronizing their operations, processing the information to be sent and collected, but in particular interacting with the user and external sources of information (websites and servers, for example). The interaction with the user consists both on the system programmability and the provision of feedback related to the liquid handling process, including its execution performances, faults, checkpoints. In one possible embodiment, the cameras and the actuators of the liquid handling android are controlled by means of USB, and a USB hub is localized inside the body. In this embodiment, a single USB cable can connect the personal computer or the tablet constituting the user interface to the liquid handling android itself. In other embodiments, a Wi-Fi connection could serve for the purpose avoiding the necessity of a physical link. The controlling software could therefore exploit USB drivers and software development kits provided with the individual components with the purpose of minimizing the development, and similarly integrate existing packages for the vision processing and for the inverse transformation determining a set of actuators angles for a given position, in angle and space, of the pipette.

An important aspect of software is constituted by the user interface. The availability of cameras capable of capturing real images of the process suggests using an approach based on virtual reality, where the user is provided with information—on the screen of the controlling system—which results partially from real images and partially from synthetic information. In this way, the adherence of the original protocol can be made in a more user-friendly way, improving the performances of the operator and reducing possible faults to minimum.

The software interface could also interact with the user during the execution of liquid handling steps. For example, a protocol could require specific liquid handling steps—or operations like spectrophotometry, phase separation, microscope inspection or similar—which cannot be executed from the android itself. Therefore, the software interface will trigger the user intervention (or in alternative simply wait for it) for example by means of visual indicators, hand waiving, acoustic signals, emails, SMS or phone calls to the user.

The purpose of the software is not limited to the execution of protocols, but it could also be extended to other operations having, for example, the purpose of improving the hardware performances. For example, it is well known in the art that accurate pipette performances require frequent calibration of the same, being the performances related to environmental parameters and also to their use. A liquid handling android could be controlled by software in such a way to execute pipette calibration procedures for example repeating a sufficient number of dispensing steps into a consumable, and monitoring (by weight, colorimetry, fluorescence or similar techniques) a physical parameter representative of the dispensed volume. It should be noted that—in a liquid handling android—there is no strict need of physically adjust the pipette calibration scale, since the software could automatically define the calibration table, and therefore the knowledge of the actual volume to be set in order to achieve a desired volume.

Having now described a few embodiments of the invention, it should be apparent to those skilled in the art that the foregoing is merely illustrative and not limiting, having been presented by way of example only. Numerous modifications and other embodiments are within the scope of ordinary skill in the art and are contemplated as falling within the scope of the invention as defined by the appended claims and equivalents thereto. The contents of any references cited throughout this application are hereby incorporated by reference. The appropriate components, processes, and methods of those documents may be selected for the present invention and embodiments thereof.

What is claimed is:

1. An apparatus for processing biological or chemical fluids, comprising
    a camera mounted on a moving arm said moving arm capable of manipulating at least one pipette, wherein said camera is capable of imaging from a plurality of locations or angles to acquire three dimensional images;
    a software interface interfacing with said moving arm allowing the manipulation and localization of the moving arm; and
    a deck area comprising a plurality of consumables, wherein camera images taken from a plurality of locations or angles to acquire three dimensional images of the deck area allow said software to perform differential analysis of the images said software interface producing data to recognize the consumables and localize the arm with respect to the consumable.

2. The apparatus according to claim 1, wherein the camera is a stereoscopic camera.

3. The apparatus according to claim 1, wherein a focus information from the images is used to extract information on the consumable height.

4. The apparatus according to claim 1, wherein a colour map of the consumables is used for the purpose of consumable identification.

5. The apparatus according to claim 1, wherein a consumable is identified by means of a tag positioned onto a consumable holder.

6. The apparatus according to claim 1, wherein the presence of a consumable is assessed by the absence of a tag within the image.

7. The apparatus according to claim 1, wherein the relative position of the arm with respect to a consumable is extracted by means of at least one property among the reconstructed position, orientation and size of a tag within the image.

8. The apparatus according to claim 7, where the distance of the camera from the consumable is reconstructed from the apparent size in the image of a tag of known real dimensions.

9. The apparatus according to claim 7, where the lateral position of the camera with respect to the consumable is measured from the apparent position of one or a plurality of tags within the image.

10. The apparatus according to claim 7, where the relative position is reconstructed from a single tag by means of its position, size and orientation within the image.

* * * * *